US008634566B2

(12) United States Patent
Latzel

(10) Patent No.: US 8,634,566 B2
(45) Date of Patent: Jan. 21, 2014

(54) METHOD FOR LOUDNESS-BASED ADJUSTMENT OF THE AMPLIFICATION OF A HEARING AID AND ASSOCIATED HEARING AID

(75) Inventor: Matthias Latzel, Eggolsheim (DE)

(73) Assignee: Siemens Medical Instruments Pte. Ltd., Singapore (SG)

(*) Notice: Subject to any disclaimer, the term of this patent is extended or adjusted under 35 U.S.C. 154(b) by 940 days.

(21) Appl. No.: 12/748,561

(22) Filed: Mar. 29, 2010

(65) Prior Publication Data

US 2010/0254538 A1    Oct. 7, 2010

(30) Foreign Application Priority Data

Apr. 2, 2009 (DE) .......................... 10 2009 016 058
Jun. 25, 2009 (DE) .......................... 10 2009 030 551

(51) Int. Cl.
    *H04R 25/00*    (2006.01)
(52) U.S. Cl.
    USPC ........................................... 381/60; 381/312
(58) Field of Classification Search
    USPC ............ 381/57, 60, 312, 321, 23.1, 316–318; 73/585
    See application file for complete search history.

(56) References Cited

U.S. PATENT DOCUMENTS

| | | | |
|---|---|---|---|
| 5,081,441 A * | 1/1992 | Chojar | 340/384.7 |
| 6,118,877 A * | 9/2000 | Lindemann et al. | 381/60 |
| 6,201,875 B1 * | 3/2001 | Davis et al. | 381/314 |
| 6,449,372 B1 | 9/2002 | Greminger | |
| 2008/0049946 A1 * | 2/2008 | Heller et al. | 381/60 |

FOREIGN PATENT DOCUMENTS

| | | |
|---|---|---|
| DE | 102006015497 A1 | 10/2007 |
| DE | 102007033484 A1 | 1/2009 |
| EP | 0661905 A2 | 7/1995 |
| EP | 0915639 A1 | 5/1999 |
| EP | 1196006 A2 | 4/2002 |
| WO | 2009010572 A1 | 1/2009 |

OTHER PUBLICATIONS

Kiessling, Jürgen, et al., "Adaptive Fitting of Hearing Instruments by Category Loudness Scaling (ScalAdapt)," Scand Audiol 25, pp. 153-160, 1966.

* cited by examiner

*Primary Examiner* — Suhan Ni
(74) *Attorney, Agent, or Firm* — Laurence A. Greenberg; Werner H. Stemer; Ralph E. Locher

(57) ABSTRACT

A method and an associated hearing aid for loudness-based adjustment of the amplification of the hearing aid by presenting test signals of a predefinable level and predefinable frequency. Blind signals are presented before and between the test signals, but the blind signals are not taken into account for the adjustment of the amplification of the hearing aid at the predefinable level and predefinable frequency. A method for binaural loudness-based adjustment of the amplification of a left hearing aid and a right hearing aid is also specified. An advantage of the invention is that it is easier for a hearing aid wearer to rank the presented test signals in his individual loudness value system and to assess them accordingly.

14 Claims, 5 Drawing Sheets

METHOD FOR LOUDNESS-BASED ADJUSTMENT OF THE AMPLIFICATION OF A HEARING AID AND ASSOCIATED HEARING AID

CROSS-REFERENCE TO RELATED APPLICATION

This application claims the priority, under 35 U.S.C. §119, of German patent applications DE 10 2009 016 058.2, filed Apr. 2, 2009, and DE 10 2009 030 551.3, filed Jun. 25, 2009; the prior applications are herewith incorporated by reference in their entirety.

BACKGROUND OF THE INVENTION

Field of the Invention

The invention lies in the field of hearing aids. More specifically, the invention pertains to a method for loudness-based adjustment of the amplification of a hearing aid by presenting test signals and to a method for loudness-based binaural adjustment of the amplification of a right hearing aid and a left hearing aid. The invention further pertains to a hearing aid that generates the blind and test signals for loudness-based adjustment of the amplification of a hearing aid and to combined left and right hearing aids that generate the blind and test signals for loudness-based adjustment of the amplification of the left and right hearing aid.

The optimum amplification of a hearing aid to compensate for hearing loss is conventionally determined by loudness scales or hearing threshold-based prescriptive adjustment formulae. The adjustment of hearing aids by means of loudness scales is a complex procedure and does not always lead to optimum adjustments. There are therefore methods in which a hearing aid wearer is interactively involved in the adjustment. This reduces and simplifies the adjustment time and optimizes adjustment in a structured manner.

Such methods are either carried out with a hearing aid acoustician in a simulated acoustic environment or in the everyday environment of the hearing aid wearer, the hearing aid being adjusted and it being possible to then test it in everyday life.

A known adaptive method for adjusting a hearing aid is the "ScalAdapt method" that was described as far back as in the 1990s in J. Kiessling et al., "Adaptive Fitting of Hearing Instruments by Category Loudness Scaling (ScalAdapt)," Scand Audiol 1996; 25; 153-60. While in the described version the adjustment signals were presented in the free field, in a commercial version the test signals were generated first hand in the hearing aid and presented to a hearing aid wearer. The method failed to become commercially accepted, however, as it did not always lead to an optimum adjustment of the hearing aids.

SUMMARY OF THE INVENTION

It is accordingly an object of the invention to provide a loudness-based adjustment method for adjusting the amplification of a hearing aid which overcomes the disadvantages of the heretofore-known devices and methods of this general type and which provides for an improved method and an improved hearing aid for adjusting the amplification of the hearing aid as a function of the hearing capacity of a hearing aid wearer.

With the foregoing and other objects in view there is provided, in accordance with the invention, a method of loudness-based adjustment of an amplification of a hearing aid, the method which comprises:

presenting test signals of a predefined level and a predefined frequency;

presenting blind signals before and/or between the test signals; and adjusting the amplification of the hearing aid on a basis of the test signals, but without taking into account the blind signals in adjusting the amplification of the hearing aid at the predefined level and the predefined frequency.

The fundamental concept of the invention lies in presenting blind signals ("dummy presentations") in addition to test signals in a loudness-based adjustment of the amplification of hearing aids. The blind signals are not used for adjusting the amplification. The frequencies and levels of the blind signals may be randomly distributed. A loudness evaluation of the blind signals can be used for subsequent adjustments and adjustment steps. They are therefore intermediately stored, or buffered.

The invention thus is a method for loudness-based adjustment of the amplification of a hearing aid by presenting test signals of a predefinable level and predefinable frequency. Blind signals are presented between the test signals, the blind signals not being taken into account for adjustment of the amplification of the hearing aid at the predefinable level and predefinable frequency. The blind signals are what are known as "dummy presentations." The advantage of this is that it is easier for a hearing aid wearer to rank the presented test signals in his individual loudness value system and to assess them accordingly.

In a development the blind signals can have different levels. This makes the anchor point more secure.

In a further embodiment the blind signals can be broadband.

In accordance with another feature of the invention, the blind signals are narrow band signals and they have different frequencies.

The levels and/or frequencies of the blind signals are also randomly set. This has the advantage that the absolute anchor is not lost during adjustment and therefore the loudness evaluations of the hearing aid wearer remain accurate. This avoids adjustment of the hearing aid in an incorrect direction.

In a development of the method a loudness evaluation of the blind signals can be used for adjusting the hearing aid at additional predefinable levels and frequencies in subsequent adjustment steps and/or adjustments. The advantage of this is that adjustment of the amplification is accelerated for additional levels and/or frequencies.

In a further embodiment the blind and test signals may be generated in the hearing aid. The advantage of this is simple adjustment of the amplification of hearing aids.

With the above and other objects in view there is also provided a method for loudness-based binaural adjustment of the amplification of a right hearing aid and a left hearing aid. In this case firstly the amplification of the right or left hearing aid is adjusted according to the inventive monaural method. The amplification of the other hearing aid is then adjusted by presenting test signals. The advantage of this is that the amplifications of the two hearing aids are optimally coordinated with each other.

In a further embodiment the adjustment of the amplification of the other hearing aid can be ended if the amplified test signals of the left and right hearing aids are perceived by a hearing aid user to be equally loud.

With the above and other objects in view there is also provided, in accordance with the invention, a hearing aid that generates the blind signals and test signals for loudness-based adjustment of the amplification of a hearing aid as summarized in the foregoing and emits the signals in an amplified manner accordingly.

In a preferred embodiment the hearing aid can include a noise generator for generating the blind and test signals.

The invention also includes a left hearing aid and a right hearing aid that generate the blind and test signals for loudness-based adjustment of the amplification of the left and right hearing aid as claimed in the inventive method and emit the signals in an amplified manner.

In a development the left and right hearing aids can be fitted with a noise generator for generating the blind and test signals.

Other features which are considered as characteristic for the invention are set forth in the appended claims.

Although the invention is illustrated and described herein as embodied in a method for loudness-based adjustment of the amplification of a hearing aid and associated hearing aid, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
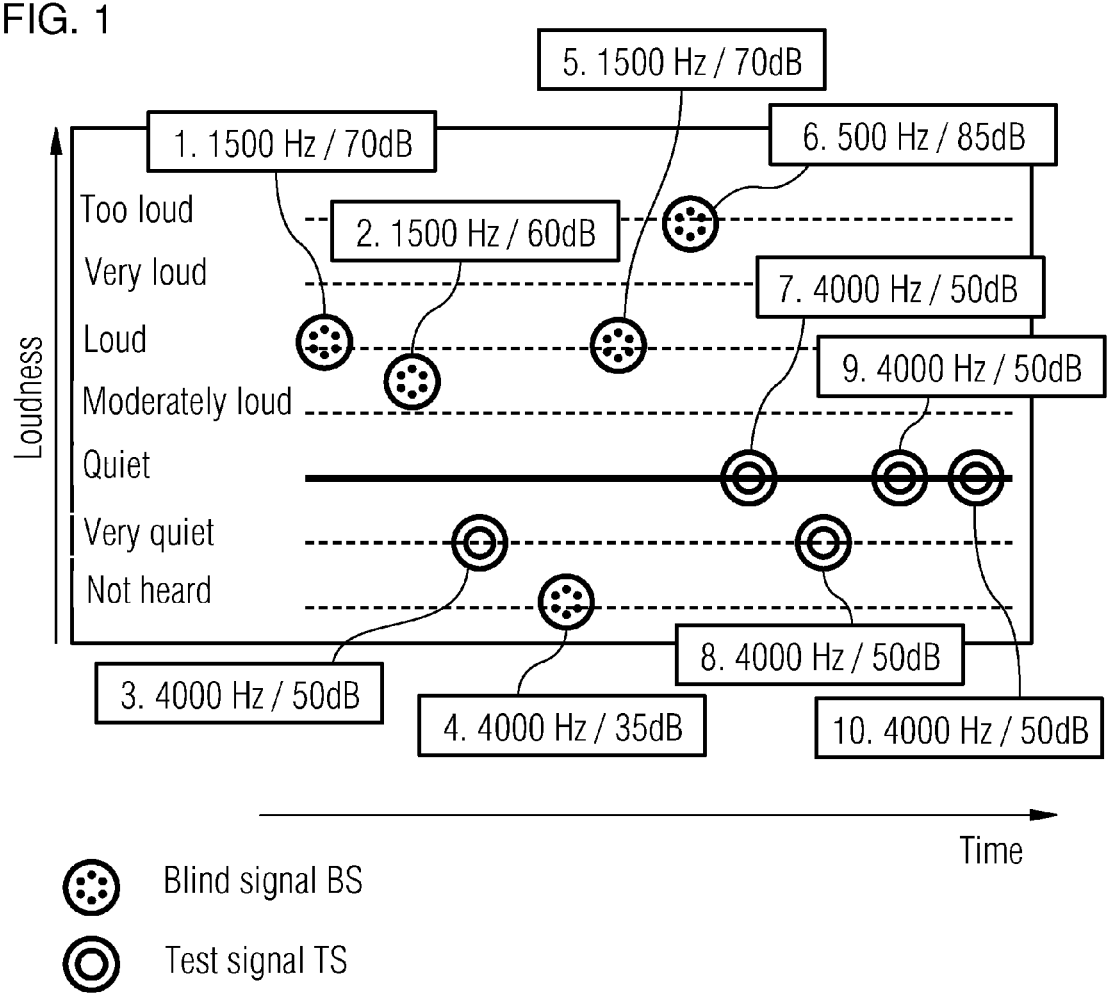
FIG. 1 shows a flow diagram illustrating a monaural narrow-band adjustment of a hearing aid.

Referring now to the figures of the drawing in detail and first, particularly, to FIG. 1 thereof, there is shown a flow diagram of a monaural narrow-band adjustment of the amplification of a hearing aid. For this purpose a narrow-band noise in accordance with predefinable frequencies and levels is generated in the hearing aid by way of a noise generator. The frequencies and levels can be selected in accordance with national or international standards relating to the loudness-based adjustment of hearing aids. Blind signals BS and test signals TS are formed from the narrow-band noise. These are amplified in accordance with the adjusted amplification of the hearing aid and presented to a wearer of the hearing aid for a loudness evaluation. Alternatively, the blind and test signals BS, TS may also be emitted in the free field by an external source.

According to the invention blind signals BS are also presented in addition to test signals TS, which are used for an adjustment of the amplification, in order to give the hearing aid wearer an absolute anchor point for loudness orientation. The levels of what are known as "dummy presentations" are preferably at the lower or upper end of the volume range and are randomly selected. It is consequently easier for the hearing aid wearer to rank the presented test signals TS in his individual loudness value system and to evaluate them according to a scale ranging from "not heard" to "too loud." The loudness evaluations of the blind signals BS are rejected, however, and are not included in adjustment of the amplification.

The frequencies of the blind signals BS are randomly selected according to the invention, so the absolute anchor is not lost to the hearing aid wearer during adjustment of the hearing aid.

Referring once more to FIG. 1, there is shown by way of example the monaural adjustment of a hearing aid for a narrow-band test signal TS of 4000 Hz and a "quiet" level of 50 dB. The x direction indicates the time and the y direction the loudness evaluation by the hearing aid wearer. The numbers 1. to 10. designate adjustment steps. In the 1st step a loud blind signal BS with a frequency of 500 Hz and a sound pressure level of 70 dB is presented as the anchor. The evaluation "loud" is not included in adjustment of the amplification. In the $2^{nd}$ step a blind signal BS is again presented, differing from the $1^{st}$ step with a level of 60 dB and a frequency of 1500 Hz. The $3^{rd}$ step presents the first test signal TS with a frequency of 4000 HZ and a level of 50 dB. The hearing aid wearer evaluates the test signal TS from the $3^{rd}$ step as "very quiet," so the amplification in the hearing aid is increased. In the $4^{th}$ step a further blind signal BS is presented with 4000 Hz and a level of 35 dB. The blind signal of the $4^{th}$ step is not heard by the hearing aid wearer. In the following $5^{th}$ step a blind signal BS is presented at 1500 Hz and a level of 70 dB. The hearing aid wearer rates the loudness as "loud." A further blind signal BS is presented in the $6^{th}$ step. It has a level of 85 dB and a frequency of 500 Hz and is rated by the hearing aid wearer as "too loud." The quiet test signal TS with frequency 4000 Hz and level 50 dB is presented in each of the following four steps. The test level TS is evaluated as quiet in the $7^{th}$ step, the amplification is therefore kept constant. When presented again in the $8^{th}$ step the test signal TS is rated as "very quiet, so amplification of the hearing aid is increased. In the $9^{th}$ and $10^{th}$ steps the test signal TS is evaluated as "quiet," so the adjustment process is ended. The target category "quiet" was "met" twice in succession. The required change in amplification is calculated from the distance of the hearing aid wearer's evaluation from the target category in each case.

Following the successful adjustment of the amplification for the loudness category "quiet," the amplification of the hearing aid is adjusted for a different loudness category and different frequency. The method is repeated until the amplifications are adjusted for all predefined loudness categories and frequencies.

Figure 2:
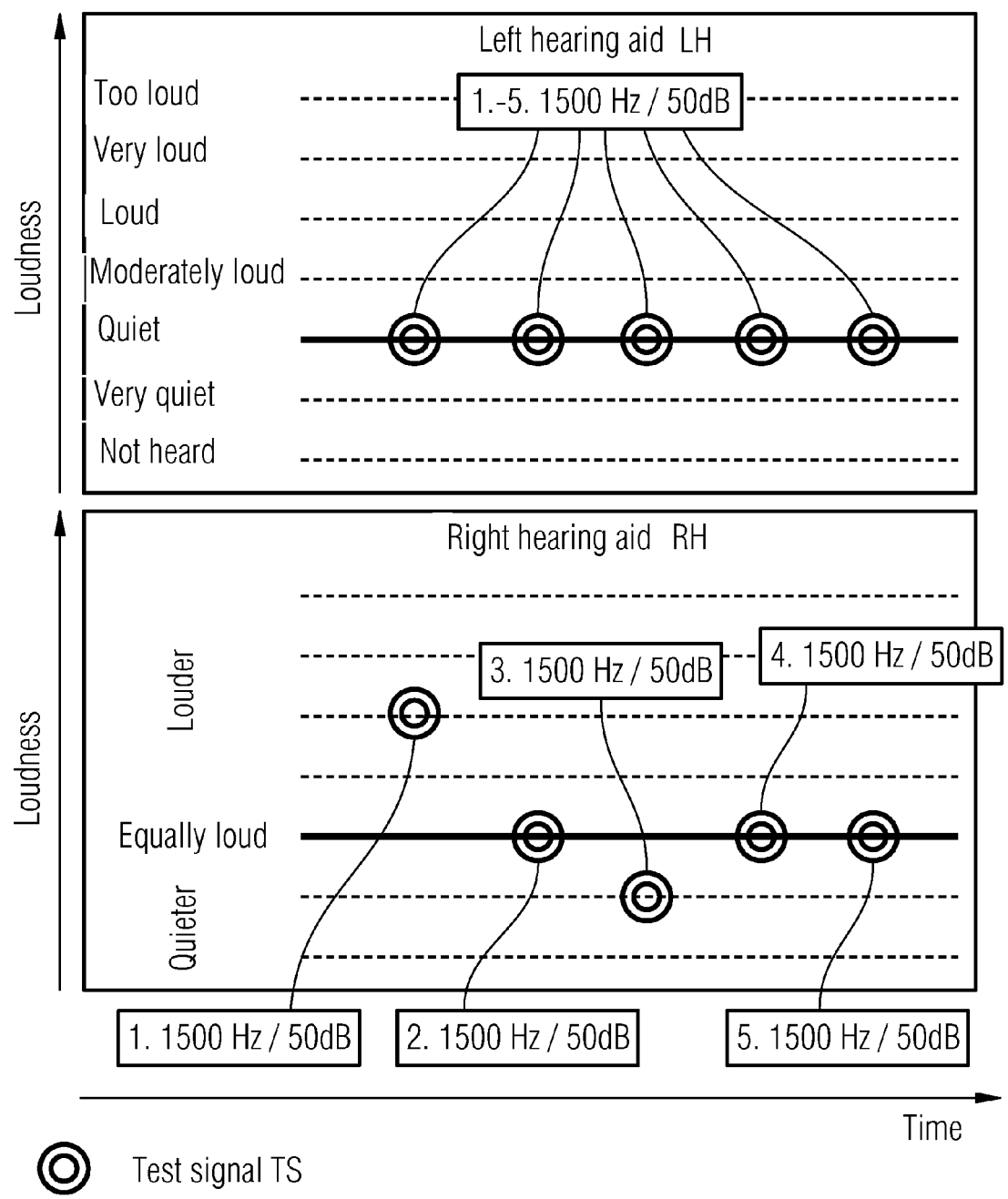
FIG. 2 shows a flow diagram illustrating a binaural narrow-band adjustment of a hearing aid.

FIG. 2 shows, by way of example, the binaural adjustment of a right hearing aid and a left hearing aid RH, LH for a narrow-band test signal TS of 1500 HZ and a "quiet" level of 50 dB. The x axis and the y axis of the graph again indicate the time and loudness respectively. Firstly, as described in FIG. 1, the left hearing aid HG is adjusted. A simultaneous presentation of test signals TS at 1500 Hz and 50 dB then takes place through the left and right hearing aids LH, RH. The hearing aid user evaluates whether the loudness of the right hearing aid RH is "louder" or "quieter" than the loudness of the left hearing aid LH or whether both hearing aids LH, RH are perceived to be "equally loud."

The x direction in FIG. 2 indicates the time and the y direction the loudness evaluation by the hearing aid wearer. Numbers 1. to 5. designate adjustment steps. The loudness of the right hearing aid HG is evaluated as "louder" in the $1^{st}$ step, so the amplification of the right hearing aid HG is reduced. The loudness is evaluated as "equally loud" in the $2^{nd}$ step; the amplification is kept constant. In the following $3^{rd}$ step the loudness is evaluated as "quieter." The amplification is increased. In the $4^{th}$ and $5^{th}$ steps the loudness is evaluated as "equally loud," so the amplification is kept constant. As both hearing aids LH, RH are evaluated as being "equally loud" twice in succession the adjustment process is successfully ended.

Following successful binaural adjustment of the amplification for the loudness category "quiet" and the frequency 1500 Hz, the amplification of the right hearing aid is adjusted for a different loudness category and different frequency. The method is repeated until the amplifications of the right hearing aid RH are adjusted for all predefined loudness categories and frequencies. The condition for this is that the left hearing aid LH has been adjusted for all frequencies and loudnesses.

The method for loudness-based binaural adjustment of the amplification can of course also start with a monaural adjustment of the right hearing aid RH with the left hearing aid LH then being binaurally adjusted.

Figure 3:
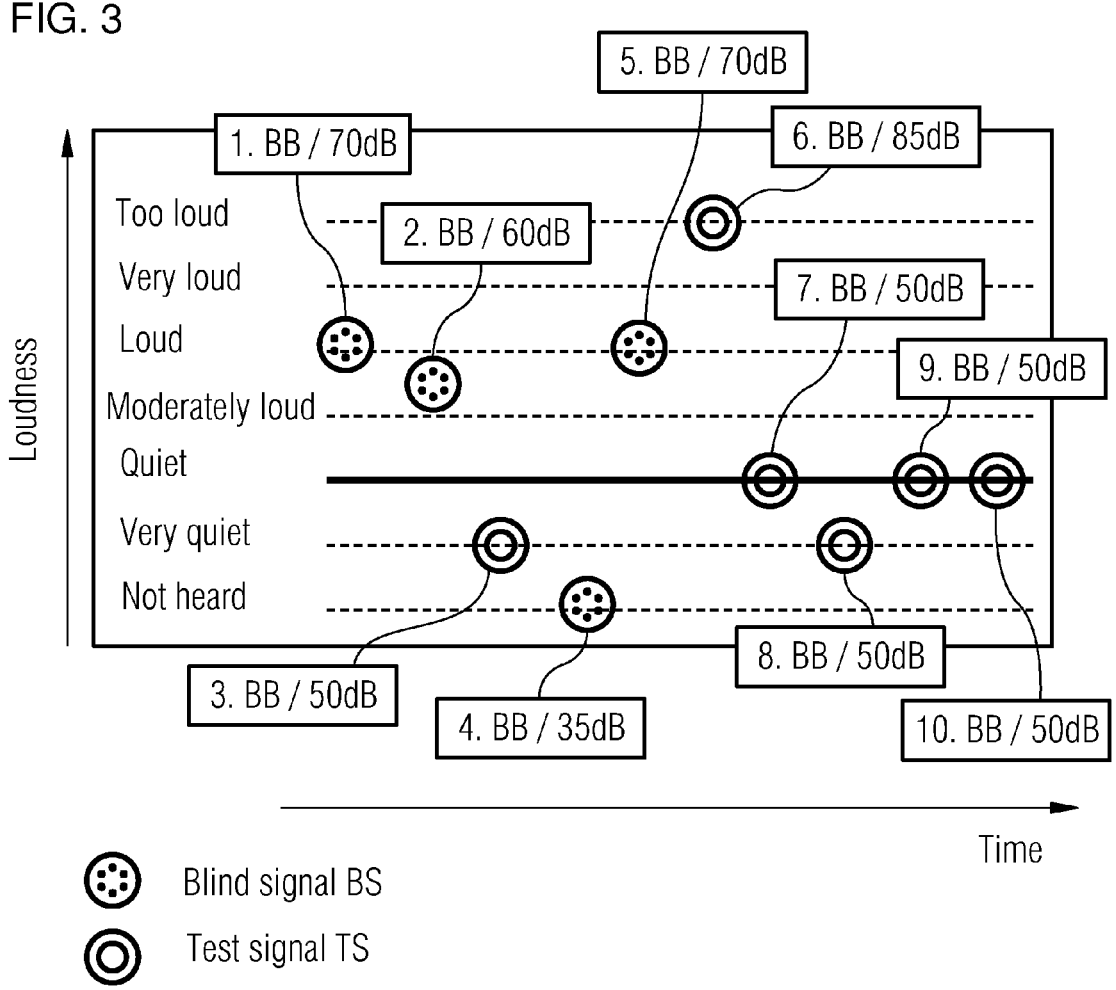
FIG. 3 shows a flow diagram illustrating a monaural broadband adjustment of a hearing aid.

FIG. 3 shows a flow chart of a monaural broadband adjustment of the amplification of a hearing aid. For this purpose a broadband noise is generated in accordance with a predefinable level, for example in the hearing aid itself, by means of a noise generator. The levels can be selected in accordance with national or international standards relating to loudness-based adjustment of hearing aids. Blind signals BS and test signals are formed from the broadband noise. These are amplified in accordance with the adjusted amplification of the hearing aid and presented to the wearer of the hearing aid for a loudness evaluation. Alternatively, the blind and test signals BS, TS may also be emitted by an external source.

According to the invention blind signals BS are also presented in addition to test signals TS, which are used for an adjustment of the amplification, in order to give the hearing aid wearer an absolute anchor point for a corresponding loudness orientation. The levels of what are known as "dummy presentations" are preferably at the lower or upper end of the volume range and are randomly selected. It is consequently easier for the hearing aid wearer to rank the presented test signals TS in his individual loudness value system and to evaluate them according to a scale from "not heard" to "too loud." The loudness evaluations of the blind signals BS are rejected, however, and are not included in the adjustment of the amplification.

FIG. 3 shows, by way of example, the monaural adjustment of a hearing aid for a broadband test signal TS with a "quiet" level of 50 dB. The x direction indicates the time and the y direction the loudness evaluation by the hearing aid wearer. Numbers 1. to 10. designate adjustment steps. A blind signal BS with 70 dB sound pressure level is presented as the anchor in the $1^{st}$ step. The evaluation "loud" is not included in adjustment of the amplification. A blind signal BS is again presented in the $2^{nd}$ step, differing from the $1^{st}$ step with a level of 60 dB. The $3^{rd}$ step presents the first test signal TS with a level of 50 dB. The hearing aid wearer evaluates the tests signal TS of the $3^{rd}$ step as "very quiet," so the amplification of the hearing aid is increased. A further blind signal BS with a level of 35 dB is presented in the $4^{th}$ step. The blind signal BS of the $4^{th}$ step is not heard by the hearing aid wearer. A blind signal BS with a level of 70 dB is presented in the following $5^{th}$ step. The hearing aid wearer rates the loudness as "loud." An additional blind signal BS is presented in the $6^{th}$ step. It has a level of 85 dB and is rated by the hearing aid wearer as "too loud." The test signal TS with level 50 dB is presented in each of the following four steps. The test signal TS is evaluated as "quiet" in the $7^{th}$ step, the amplification is therefore kept constant. With repeated presentation in the $8^{th}$ step the test signal TS is rated "very quiet," so the amplification of the hearing aid is increased. The test signal TS is rated "quiet" in the $9^{th}$ and $10^{th}$ steps, so the adjustment process is ended. The target category "quiet" was "met" twice in succession. The change in amplification required in each case is calculated from the distance of the hearing aid wearer's evaluation from the target category.

Following successful adjustment of the amplification for the loudness category "quiet," the amplification of the hearing aid is adjusted for a different loudness category. The method is repeated until the amplifications are adjusted for all predefined loudness categories.

Figure 4:
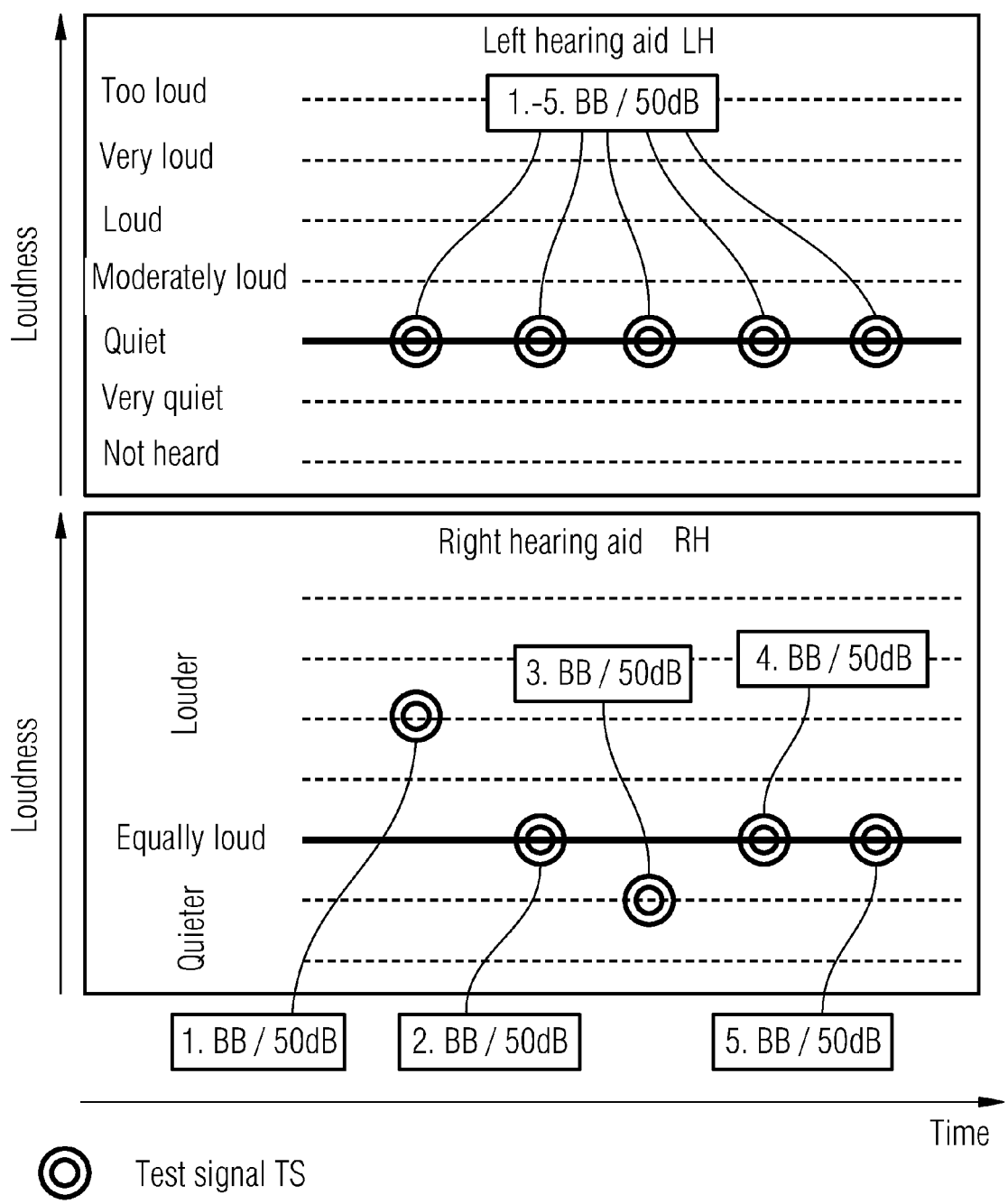
FIG. 4 shows a flow diagram illustrating a binaural broadband adjustment of a hearing aid.

FIG. 4 shows, by way of example, the binaural adjustment of a right hearing aid and a left hearing aid RH, LH for a broadband test signal TS with a "quiet" level of 50 dB. The x axis and the y axis of the graph again indicate the time and loudness respectively. Firstly, as described in FIG. 3, the left hearing aid HG is adjusted. A simultaneous presentation of test signals TS at 50 dB then takes place through the left and right hearing aids LH, RH. The hearing aid user evaluates whether the loudness of the right hearing aid RH is "louder" or "quieter" than the loudness of the left hearing aid LH or whether both hearing aids LH, RH are perceived to be "equally loud."

The x direction in FIG. 4 indicates the time and the y direction the loudness evaluation by the hearing aid wearer. Numbers 1. to 5. designate adjustment steps. The loudness of the right hearing aid RH is evaluated as "louder" in the $1^{st}$ step, so the amplification of the right hearing aid RH is reduced. The loudness is evaluated as "equally loud" in the $2^{nd}$ step; the amplification is kept constant. In the following $3^{rd}$ step the loudness is evaluated as "quieter." The amplification is increased. In the $4^{th}$ and $5^{th}$ steps the loudness is evaluated as "equally loud," so the amplification is kept constant. As both hearing aids LH, RH are evaluated as being "equally loud" twice in succession the adjustment process is successfully ended.

Following successful binaural adjustment of the amplification for the loudness category "quiet," the amplification of the right hearing aid is adjusted for a different loudness category. The method is repeated until the amplifications of the right hearing aid RH are adjusted for all predefined loudness categories.

The method for loudness-based binaural adjustment of the amplification can of course also start with a monaural adjustment of the right hearing aid RH with the left hearing aid LH then being binaurally adjusted.

Figure 5:
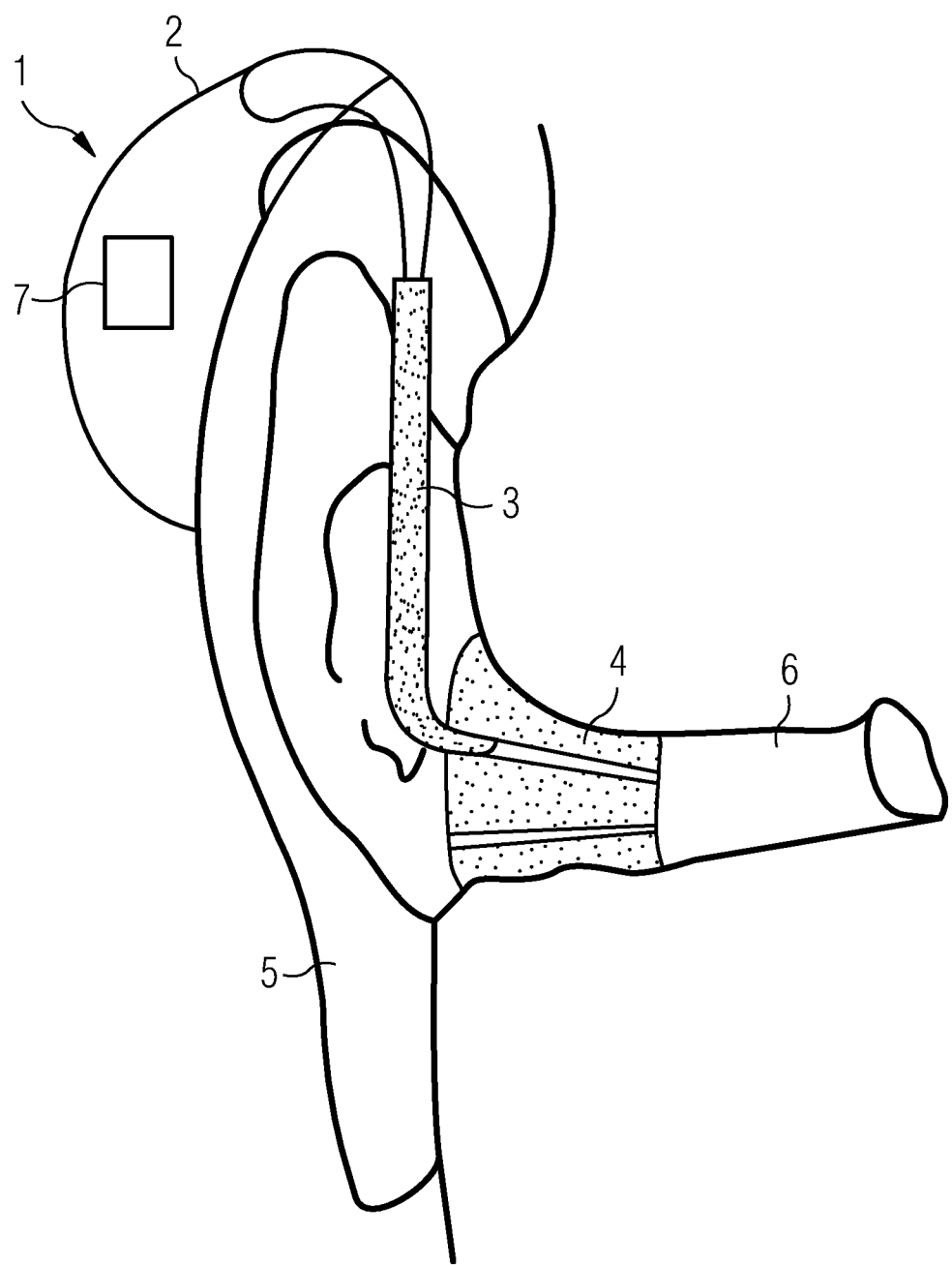
FIG. 5 is a view of a human ear with a behind-the-ear hearing aid.

FIG. 5 schematically shows an inventive behind-the-ear hearing aid 1 comprising a hearing aid case 2, a sound tube 3 and an otoplastic 4. The hearing aid case 2 sits behind a hearing aid wearer's ear 5. The hearing aid case 2 is connected to the sound tube 3. The sound tube 3 terminates with the otoplastic 4 which fixes the sound tube 3 in the auditory canal 6 of the hearing aid wearer. A noise generator 7, which generates the narrow-band and broadband noise signals that are used for presenting blind and test signals as discussed with reference to the process of FIGS. 1 to 4, is arranged in the hearing aid case 2. As noted above, the sound/noise source may also be a hearing aid-external source.

The two hearing aids LH, RH can exchange data via radio communication for a binaural coupling of the left and right hearing aids LH, RH.

Loudness evaluations of blind signals at a certain frequency and/or level can be used for simplified adjustment of the amplification at a different level and/or different frequency.

The invention claimed is:

1. A method of loudness-based adjustment of an amplification of a hearing aid, the method which comprises:
    presenting test signals of a predefined level and a predefined frequency;
    presenting blind signals before and/or between the test signals; and
    adjusting the amplification of the hearing aid on a basis of the test signals, but without taking into account the blind signals in adjusting the amplification of the hearing aid at the predefined level and the predefined frequency.

2. The method according to claim 1, which comprises providing the blind signals at different levels.

3. The method according to claim 1, wherein the blind signals are broadband signals.

4. The method according to claim 1, wherein the blind signals are narrow band signals and have different frequencies.

5. The method according to claim 1, which comprises randomly selecting at least one of a level and a frequency of each blind signal.

6. The method according to claim 1, which comprises using a loudness evaluation of the blind signals for adjustment of the hearing aid at additional predefinable levels and frequencies.

7. The method according to claim 1, which comprises generating the blind signals and the test signals in the hearing aid.

8. A method of loudness-based binaural adjustment of an amplification of a right hearing aid and a left hearing aid, the method which comprises:
    adjusting an amplification of one of the right or left hearing aid according to the method according to claim 1; and
    adjusting an amplification of the respectively other one of the right or left heating aid by presenting test signals.

9. The method according to claim 8, which comprises terminating the adjustment of the amplification of the other hearing aid if the amplified test signals of the left and right hearing aids are perceived by a hearing aid user to be equally loud.

10. A hearing aid configured to generate the blind signals and the test signals for loudness-based adjustment of the amplification of a hearing aid according to claim 1 and to emit the signals in an amplified manner.

11. A hearing aid with loudness-based adjustment of an amplification of the hearing aid, comprising:
    a noise generator for generating blind signals and test signals;
    means for presenting the test signals at a predefined level and a predefined frequency to a wearer of the hearing aid and for presenting the blind signals before and/or between the test signals; and
    wherein the amplification of the hearing aid is adjusted on a basis of the test signals, but without taking into account the blind signals in adjusting the amplification of the hearing aid at the predefined level and the predefined frequency.

12. Left and right hearing aids configured to generate the blind signals and the test signals for loudness-based adjustment of the amplification of the left and right hearing aid according to claim 8, and to emit the signals in an amplified manner.

13. The left and right hearing aids according to claim 12, comprising a noise generator for generating the blind signals and the test signals.

14. A method of loudness-based adjustment of an amplification of a hearing aid, the method which comprises:
    presenting test signals of a predefined level and a predefined frequency;
    presenting blind signals having a given level and a given frequency before and/or between the test signals; and
    adjusting the amplification of the hearing aid on a basis of the test signals, but without taking into account the blind signals in adjusting the amplification of the hearing aid at the predefined level and the predefined frequency.

* * * * *